United States Patent [19]

Gilbert

[11] 4,028,425
[45] June 7, 1977

[54] CONTINUOUS PROCESS FOR CONCURRENT PRODUCTION OF DINITROTOLUENE AND HIGH-STRENGTH NITRIC ACID

[75] Inventor: Everett E. Gilbert, Morristown, N.J.

[73] Assignee: The United States of America as represented by the Secretary of the Army, Washington, D.C.

[22] Filed: June 1, 1976

[21] Appl. No.: 691,912

[52] U.S. Cl. .................................. 260/645; 423/393
[51] Int. Cl.$^2$ ................... C07C 79/10; C01B 21/38
[58] Field of Search ..................... 260/645; 423/393

[56] References Cited

UNITED STATES PATENTS

| 3,243,466 | 3/1966 | Brogden et al. | 260/645 |
| 3,981,933 | 9/1976 | Cook et al. | 260/645 |

Primary Examiner—Leland A. Sebastian
Attorney, Agent, or Firm—Nathan Edelberg; A. Victor Erkkila

[57] ABSTRACT

Dinitrotoluene and nitric acid are concurrently produced by continuously introducing toluene, nitrogen dioxide and oxygen in a molar ratio of at least 4 mols nitrogen dioxide and 1 mol oxygen per mol toluene into a reaction zone containing a reaction medium comprising dinitrotoluene and 93–103% nitric acid, maintaining the resulting mixture of toluene, nitrogen dioxide, oxygen and reaction medium under a pressure of at least 100 psig and at a temperature up to about 100° C. until a reaction product containing dinitrotoluene and 93–103% nitric acid in the ratio of about 1 mol dinitrobenzene and 2 mols nitric acid is produced, and continuously removing said reaction product from the reaction zone.

6 Claims, No Drawings

CONTINUOUS PROCESS FOR CONCURRENT PRODUCTION OF DINITROTOLUENE AND HIGH-STRENGTH NITRIC ACID

GOVERNMENTAL INTEREST

The invention described herein may be manufactured, used and licensed by or for the Government for Governmental purposes without the payment to me of any royalties thereon.

BACKGROUND OF THE INVENTION

Dinitrotoluene is usually prepared by nitrating toluene with a mixture of nitric and sulfuric acids ("mixed acid"), as described in "The Chemistry of Powder and Explosives," by T. L. Davis, pg. 148, in "Methoden der Organischen Chemie (Houben-Weyl), " Vol. X/1, pg. 525, and in Interscience Encyclopedia, Vol. 13, pg. 851. This procedure involves the removal of water by the use of sulfuric acid, the recovery of which adds to the cost and presents a pollution and disposal problem. The elimination of sulfuric acid in nitration with azeotropic removal of the water by heating the hydrocarbon, or partially nitrated hydrocarbon, with a diluent acting as an entraining agent for the water has been described by Kokatnur in U.S. Pat. Nos. 2,435,314 and 2,435,544 (1948). The mononitration of toluene by this method has been studied by Othmer and Kleinhans (Ind. Eng. Chem. 36,477 (1944)). A somewhat similar approach was used by Crater (U.S. Pat. No. 2,362,743 (1944)), who mononitrated toluene with 70% nitric acid, separated the resulting mononitrotoluene, and then converted it to dinitrotoluene by heating it with 98% nitric acid at 80° C.

It is known to produce high-strength (98%) nitric acid by the reaction of nitrogen dioxide and oxygen with water in the presence of nitric acid according to the following reaction:

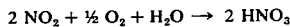

$$2 NO_2 + \tfrac{1}{2} O_2 + H_2O \rightarrow 2 HNO_3$$

There are several commercial procedures for doing this, including those of Fauser (Chem. Eng. 59(1), 238 (Jan 1952)), Peroxide (Chem. Eng., Dec. 25, 1972, pg. 50), Sumimoto (Nitrogen, No. 74, 40 (1971)), Hycon (Nitrogen, No. 79, 24 (1972)), and Sabar (European Chem. News, Aug 24, 1973, pg. 27). These procedures all employ pressure, varying from 8 atm. (Peroxide) to 52 atm. (Fauser). The Fauser process operates at 70°–75° C. and uses oxygen; the Peroxide process employs air.

SUMMARY AND DETAILED DESCRIPTION OF THE INVENTION

An object of the present invention is to provide a continuous process for the concurrent production of crude dinitrotoluene and high strength nitric acid directly from toluene without the need for the addition of water or the removal of reaction water by means of concentrated sulfuric acid or entraining agents.

Other objects will become apparent as the invention is further described.

In accordance with the present invention dinitrotoluene and high strength nitric acid are concurrently produced by continuously introducing toluene, nitrogen dioxide and oxygen in a ratio of at least about 4 mols nitrogen dioxide and 1 mol oxygen per mol of toluene into a reaction zone containing a reaction medium consisting essentially of dinitrotoluene and 93–103% nitric acid, maintaining the resulting mixture of toluene, nitrogen dioxide, oxygen and said reaction medium in the reaction zone under a pressure of at least 100 psig at a temperature up to about 100° C. until a reaction product consisting essentially of dinitrotoluene and 93–103% nitric acid in the ratio of about 1 mol dinitrotoluene and 2 mols nitric acid is produced, and continuously removing said reaction product from the reaction zone. The nitric acid formed as a coproduct in the process can be separated from the dinitrotoluene by vacuum distillation in known manner.

The production of dinitrotoluene and nitric acid as coproducts according to the present process is represented by the following overall reaction equation, wherein 4 mols of nitrogen dioxide and 1 mol of oxygen per mol of toluene are theoretically required to produce 1 mol of dinitrotoluene and 2 mols of nitric acid:

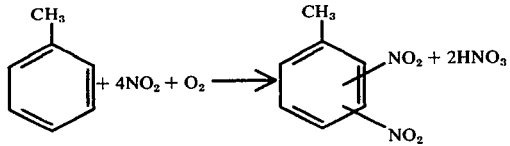

The process of the present invention is conveniently started by charging the reactor (e.g. autoclave) with the aforesaid reaction medium consisting essentially of 1 mol of dinitrotoluene (as mixed isomers) and 2 mols of nitric acid of 93–103% strength, which is the reaction product produced in the process itself. In steady-state operating conditions such reaction product is continuously removed from the reactor at a rate commensurate with the feed of the reactants so as to maintain the volume of the liquid reactor contents essentially constant. The reactor can also be initially charged with other mixtures of nitric acid and dinitrobenzene, or with only one of these components, to provide a reaction medium; but in continuous operation of the process of the present invention, the reaction medium in the reactor will eventually consist essentially of a mixture of dinitrobenzene and 93–103% nitric acid in the approximate ratio of 1 mol of dinitrobenzene and 2 mols of nitric acid. (Nitric acid of greater than 100% strength of course consists of a mixture of $HNO_3$ and $N_2O_5$.)

The suitability of the aforesaid reaction medium in the present process is shown by the following experiment, wherein crude dinitrotoluene (11 grams, 0.06 mol) and 99% nitric acid (7.6 grams, 0.12 mol) were mixed at room temperature. No reaction or heat effect was noted and the dinitrotoluene dissolved readily to yield a clear, mobile solution. When the solution was held in an ice bath at 0°–5° C. for 2 hours, no crystallization or marked increase in viscosity was noted. When the solution was heated to 95°–100° C. no more decomposition was noted than that noted by similarly heating the nitric acid in the absence of dinitrotoluene. In another experiment toluene (12 grams, 0.13 mol) was added during about 10 minutes to a mixture of crude dinitrotoluene (227 grams, 1.25 mols) and 98% nitric acid (152 grams, 2.4 mols) preheated to 70° C., during which the strongly exothermic reaction was controlled by the periodic application of cooling. When the addition was complete, the mixture was heated with agitation at 70°–75° C. for 15 minutes, cooled and drowned in water to precipitate the crude dinitrotoluene as a hard solid, which was separated by filtration. No oil was noted to pass through the filter, indicating the absence of unreacted toluene or mononitrotoluene.

The present process is generally carried out at temperatures ranging about from 0° to 100° C., preferably from 60° to 100° C. The use of reaction temperatures substantially above 100° C. promotes undesired side reactions and reduced yield and quality of dinitrotoluene and hence are not preferred.

Four mols of nitrogen dioxide and 1 mol of oxygen per mol of toluene are theoretically required for the conversion of toluene to dinitrotoluene, as noted previously. The use of lower ratios than 4 mols of nitrogen dioxide and 1 mol of oxygen per mol of toluene results in an incomplete conversion of the nitrogen dioxide to nitric acid and as well as of the toluene to dinitrotoluene and thus produces a reaction product containing dinitrotoluene along with mononitrotoluene and possibly unreacted toluene, which must be removed. The use of higher molar ratios that theory, although operative and sufficient for the complete conversion of the toluene to dinitrotoluene, results in unreacted nitrogen dioxide and oxygen which must be recovered. Nitrogen peroxide ($N_2O_4$) can be employed in place of nitrogen dioxide in similar manner with essentially equivalent results in the present process, wherein one mol of nitrogen peroxide is equivalent to two mols of nitrogen dioxide.

The present process is carried out under a superatmospheric pressure of at least 100 psig. and preferably between about 350 and 1100 psig.

The reaction time required for the production of dinitrotoluene and nitric acid of 93–103% strength is not critical and depends on various factors, principally the reaction temperature and pressure and rate of feed of the reactants. The residence time of the reactants in the reaction zone according to the present process is sufficient to complete the formation of the dinitrotoluene and the nitric acid of 93–103% strength, which can be accomplished within a few minutes, as shown in the example.

The following example illustrates a specific embodiment of the method of carrying out the process of the present invention.

EXAMPLE

Toluene, nitrogen dioxide and oxygen at the uniform hourly rates of 73 grams (0.8 mols) toluene, 146 grams (3.2 mols) nitrogen dioxide, and 25 grams (0.8 mol) oxygen are separately and continuously introduced below the surface of a preheated liquid mixture of 144 grams (0.8 mol) dinitrotoluene and 100 grams (1.6 mols) 98% nitric acid charged to an aluminum-lined, jacketed autoclave. The reaction mixture is agitated and maintained under a pressure of about 750 psig. and at a temperature of 70°–80° C. by application of heating and cooling medium in the jacket of the autoclave, as required. Reaction mixture of essentially the same composition as the original charge continuously flows out of the top of the autoclave through a pressure-reducing valve to a receiver at such a rate as to maintain an essentially constant liquid level in the autoclave. The average residence time of the reactants in the autoclave is approximately 15 minutes. The reaction product thus obtained is vacuum distilled in conventional manner to separate the crude dinitrotoluene from the 98% nitric acid contained therein.

The foregoing disclosure is merely illustrative of the principles of this invention and is not to be interpreted in a limiting sense. I wish it to be understood that I do not desire to be limited to the exact details of construction shown and described, because obvious modifications will occur to a person skilled in the art.

I claim:

1. The process of continuously producing dinitrotoluene and 93–103% nitric acid, which comprises continuously introducing toluene, nitrogen dioxide or nitrogen peroxide and oxygen into a reaction zone containing a reaction medium consisting essentially of dinitrotoluene and 93–103% nitric acid, maintaining the resulting mixture of toluene, nitrogen dioxide or nitrogen peroxide, oxygen and reaction medium under a pressure of at least 100 psig. until a reaction product consisting essentially of dinitrotoluene and 93–103% nitric acid in a mol ratio of about 2 mols of nitric acid and 1 mol of dinitrotoluene is produced, and continuously removing said reaction product from the reaction zone.

2. The process of claim 1, wherein toluene, nitrogen dioxide and oxygen are introduced in a ratio of at least about 4 mols of nitrogen dioxide and 1 mol of oxygen per mol of toluene.

3. The process of claim 2, wherein the reaction is carried out at a temperature within the range about from 0° to 100° C.

4. The process of claim 2, wherein the reaction is carried out at a temperature between about 0° and 100° C. and a pressure between about 350 psig. and 1100 psig.

5. The process of claim 2, wherein the reactants are introduced in the ratio of about 4 mols of nitrogen dioxide and about 1 mol of oxygen per mol toluene.

6. The process of claim 5, wherein the reaction is carried out at a temperature between about 70° and 80° C. under a pressure of about 750 psig.

* * * * *